United States Patent [19]

Asta

[11] Patent Number: 5,045,078
[45] Date of Patent: Sep. 3, 1991

[54] DEVICE FOR FEMALE INTERMITTENT SELF-CATHETERIZATION

[76] Inventor: Linda R. Asta, 16 Alden Pl., West Newton, Mass. 02165

[21] Appl. No.: 624,448

[22] Filed: Dec. 10, 1990

Related U.S. Application Data

[63] Continuation-in-part of Ser. No. 421,504, Feb. 6, 1990, abandoned.

[51] Int. Cl.⁵ .......................... A61F 5/44; A61B 5/00
[52] U.S. Cl. ..................... 604/329; 128/761
[58] Field of Search ................. 604/329–331; 128/76; 4/144.1–144.4

[56] References Cited

U.S. PATENT DOCUMENTS

| | | |
|---|---|---|
| 3,194,238 | 7/1965 | Breece, Jr. . |
| 4,194,508 | 3/1980 | Anderson . |
| 4,246,901 | 1/1981 | Michaud . |
| 4,563,183 | 1/1986 | Barrodale et al. . |
| 4,615,692 | 10/1986 | Giacalone et al. ................. 604/329 |
| 4,690,677 | 9/1987 | Erb ....................................... 604/329 |
| 4,846,818 | 7/1989 | Keidahl et al. . |
| 4,889,533 | 12/1989 | Beecher ............................... 604/330 |
| 4,986,823 | 1/1991 | Anderson et al. ................. 604/328 |

OTHER PUBLICATIONS

Japan Kokai Utility Application Shimoku Nakao et al., May 26, 1977.

Primary Examiner—Randall L. Green
Assistant Examiner—R. Clarke
Attorney, Agent, or Firm—Hamilton, Brook, Smith & Reynolds

[57] ABSTRACT

A catheter guide for use in female intermittent self-catheterization to assist in guiding a catheter into the urinary meatus. A hand held guide has a vaginal insert portion joined to a guiding portion at an angle. There is at least one guide hole in the guiding portion which is alignable with the meatus when the insert portion is in the vagina.

21 Claims, 3 Drawing Sheets

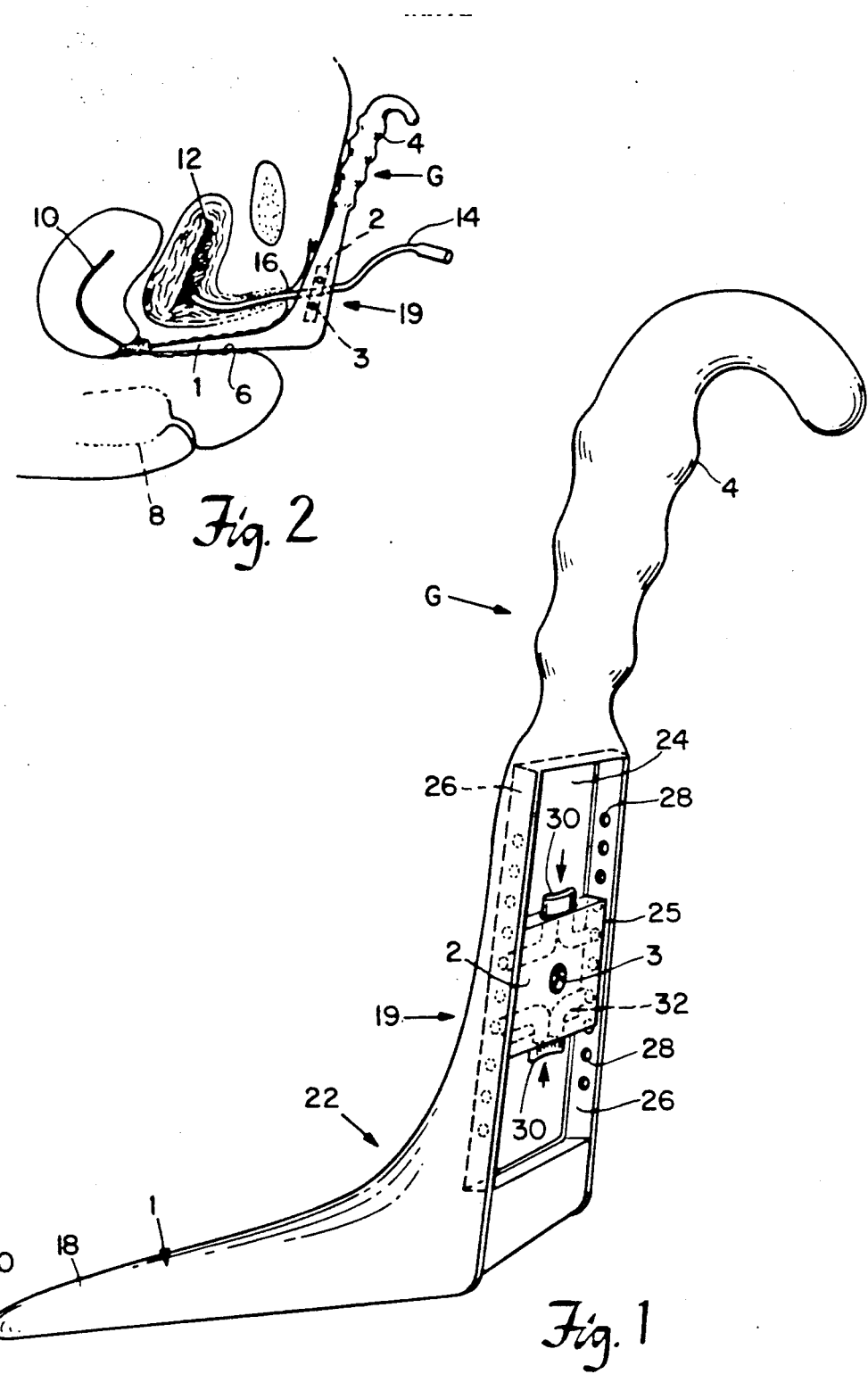

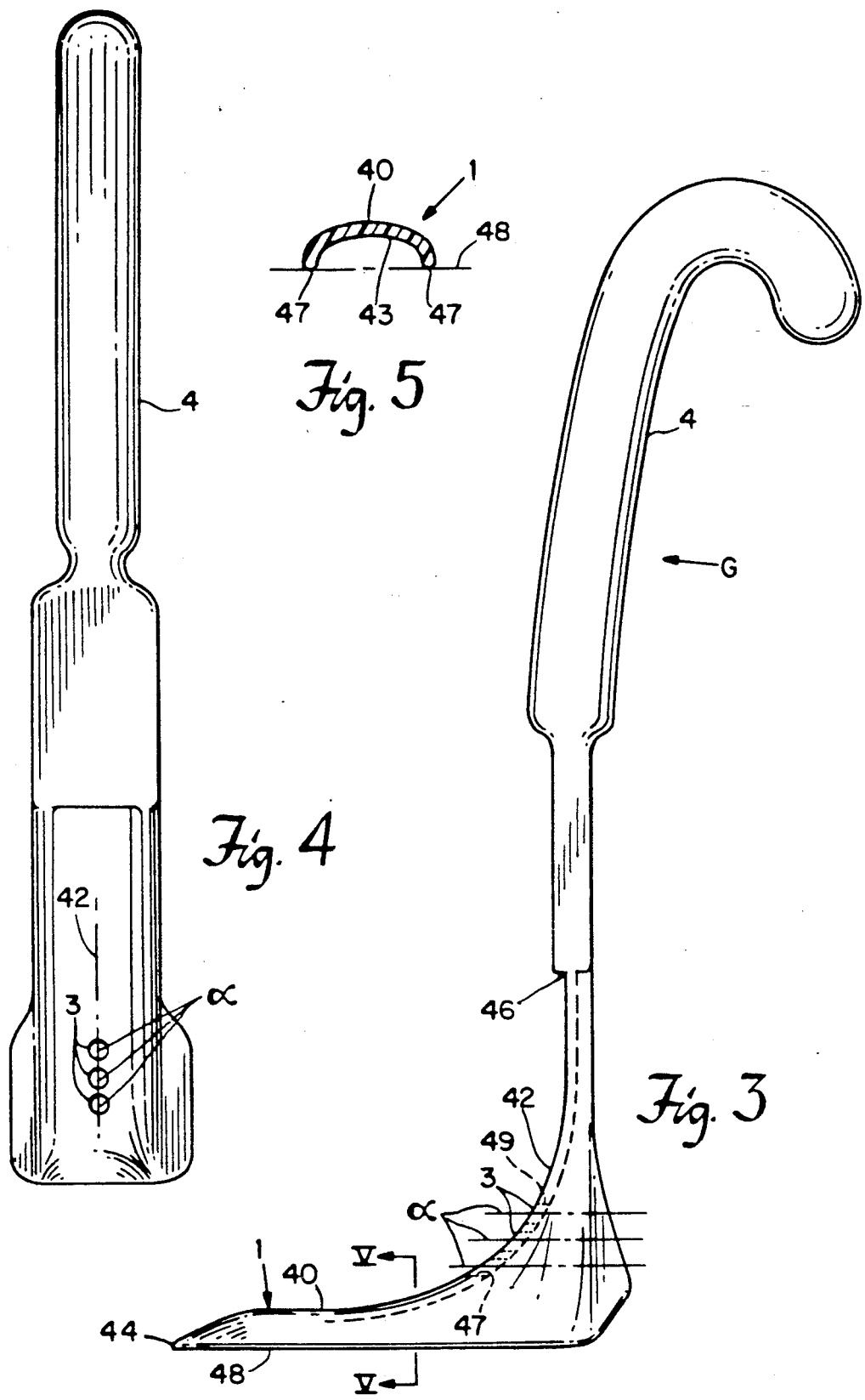

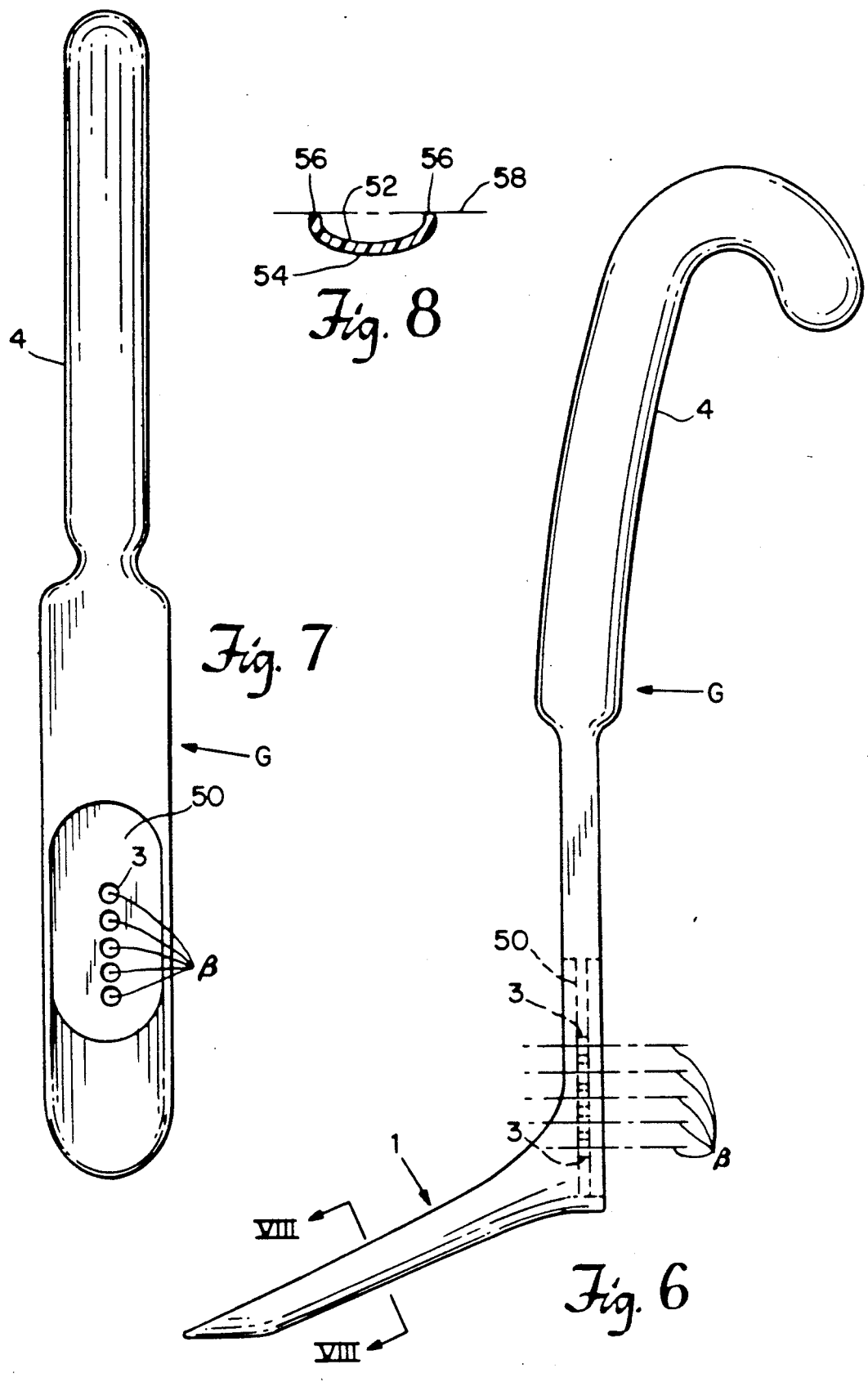

1

DEVICE FOR FEMALE INTERMITTENT SELF-CATHETERIZATION

RELATED APPLICATION

This is a Continuation-In-Part of U.S. application Ser. No. 07/421,504, filed Feb. 6, 1990 now abandoned.

FIELD OF THE INVENTION

This invention relates to medical devices to assist in the process of intermittent, self-catheterization by females. The devices are to be used by females with neurological dysfunctions of the bladder and/or other muscles and innervation associated with micturition.

BACKGROUND OF THE INVENTION

The bladder serves two functions: for storage of urine and evacuation of urine. While the two functions are related and depend upon each other, evacuation requires a short period of time and storage occupies most of the bladder's functional time. Deviation from normal bladder function constitutes symptomatology of bladder dysfunction. If a bladder cannot function as a reservoir to retain urine, the problem is known as incontinence. Conversely, if a bladder is unable to evacuate urine, the problem is called urinary retention. However, incontinence may occur once the bladder has filled to capacity and overflows. This is known as overflow incontinence. These symptoms are caused by many different disease processes. All, however, affect the mechanism of voiding, resulting in sensory or motor neurogenic-type bladders.

Neurogenic bladder disease is frequently found in paraplegia, multiple sclerosis, cerebral vascular accidents, brain injuries, spinal cord lesions, trauma, infection or disogenic disease affecting the sacral area of the spinal cord, extensive abdominal surgical operations and diabetes.

This invention relates to the problem or urinary retention and/or the inability to completely empty the bladder during micturition. Patients with urinary retention or increased post-void residuals require intermittent catheterization. Patients who can self-cathereterize then require less invasive intervention, therefore decreasing the overall expenses associated with neurogenic bladder disease.

Generally speaking, patients who require intermittent self-catheterization have lower-motor and/or sensory type neurogenic bladders that result in the retention of urine either from the inability to generate nerve impulses that contract the bladder muscle adequately or the loss of the voiding reflex arc completely. This is due to interference of nerve pathways in the brain or spinal column, or the sacral area of the spinal column where nerve impulses control detrusor function and the process of micturition.

These patients will retain large quantities or urine. They may or may not have any sensation at signalling them to intentionally urinate. The normal bladder capacity is from about 400–500 cc's, but many patients requiring intermittent catheterization generally have large bladder capacities of from about 600–1500 cc's.

If there is a malfunction of an urethral sphincter, there is potential of infected urine returning to the kidney causing a kidney stone or an infection, or bladder stones formed due to urinary stasis.

It is customary for women with lower-motor neuron type neurogenic bladders to insert a urethral catheter to void in the bathroom on a predetermined time schedule. Self-catheterization is normally performed every four to six hours because urine that remains in the bladder is prone to infection or stone formation.

Patients that have neurological dysfunction may have other neurological symptoms, as well. For example, multiple sclerosis patients often have fine-motor neuron dysfunction often accompanied by visual impairment. This makes intermittent self-catheterization difficult if not impossible since the process generally requires the ability of the patient to have fine motor skills and good vision to locate the urinary meatus.

Consequently, it is an object of the present invention to increase the potential and possibility for intermittent self-catheterization by those women with neuromuscular dysfunctions or complications resulting from other disorders which require the process of intermittent self-catheterization to aid in the function of micturition.

It is a particular object of the present invention to produce a medical device to assist in the process of intermittent self-catheterization.

SUMMARY OF THE INVENTION

The invention resides in a catheter guide for use during female, intermittent, self-catheterization for the purpose of assisting in guiding a catheter into the urinary meatus. It is embodied in a hand held guide having a vaginal insert portion which is joined to a guiding portion at an angle. There is at least one guide hole in the guiding portion which is alignable with the meatus when the insert is in the vagina. A handle is joined to the guiding portion and the parts are arranged such that the insert portion and the handle constitute the opposite ends of the hand held guide. The vaginal insert is joined to the guiding portion preferably at an obtuse junction which may be somewhat greater than 90°.

In one embodiment of the invention, the guiding portion is adjustable toward and away from the insert portion and utilizes a single guiding hole.

In another embodiment of the invention, there is a plurality of guide holes linearly arranged in the guiding portion. The surface of the insert portion closest to the guiding portion may be made concave, convex, or flat.

The invention also contemplates a plurality of guide holes formed in either a planar surface of the guiding portion or a curvilinear surface of the guiding portion depending upon the shape and configuration of the insert portion.

The invention also contemplates a non-adjustable device having but a single guide hole which is one of a series of devices wherein the guide holes vary in spacing from the insert portion.

The above and other features of the invention including various novel details of construction and combinations of parts will now be more particularly described with reference to the accompanying drawings and pointed out in the claims. It will be understood that the particular device for female intermittent self-catheterization is shown by way of illustration only and not as limitation of the invention. The principle and features of this invention may be employed in varied and numerous embodiments without departing from the scope of the invention.

BRIEF DESCRIPTION OF THE DRAWINGS

The foregoing and other objects, features and advantages of the invention will be apparent from the follow- FIG. 1 is a three dimensional view of one embodiment of the invention;

FIG. 2 is an anatomical cross sectional view of the female anatomy (pelvic region) with the FIG. 1 embodiment of the invention inserted in place;

FIG. 3 is a side view of a second embodiment of the invention;

FIG. 4 is a front view thereof;

FIG. 5 is a section taken along line V—V on FIG. 3;

FIG. 6 is a side view of another embodiment of the invention;

FIG. 7 is a front view thereof; and

FIG. 8 is a section taken along line VIII—VIII on FIG. 6.

DETAILED DESCRIPTION OF THE INVENTION

Referring to FIG. 1, an embodiment of catheter guide G is shown including a vaginal insert generally designated 1, an adjustment mechanism 2, an alignment hole 3 and a handle 4. The adjustment mechanism 2 and its hole 3 are part of guide G known as the guiding portion. FIG. 2 shows the guide G in inserted position with the insert 1 in the vagina 6. This is shown in position relative to the rectum 8, the uterus 10 and the bladder 12. A catheter 14, approximately 4 inches long, the end of which passes through alignment hole 3 in the adjustment mechanism 2 and into the urinary meatus 16 through the urethra and into the bladder. It may be a Foley-type catheter or a plastic type urethral catheter.

The guide G may be made of any surgically acceptable material preferably plastic. It is relatively thin walled to reduce weight. The insert portion 1 is an elongate, tapered guide having an arcuate or convex upper surface 18 proximate the guiding portion generally designated 19. It tapers from the tip 20 in a gradual concave configuration 22 which ultimately terminates at the handle 4.

A rectangular opening 24 accommodates the adjustment mechanism 2, which includes a plate 25, between sidewalls 26 for adjustable vertical movement. Detent holes 28 are formed in the sidewalls 26. The adjustment mechanism 2 is raised and lowered by urging a pair of pressure members 30 toward each other in the direction of the arrows. Each pressure member is connected to a pair of flexible detents 32 which are withdrawn from the detent holes 28 which are spaced approximately .5 centimeters apart when the members 30 are urged toward each other. At this time, the adjustment plate 25 can be moved vertically in the guide opening 24. Upon release of the members 30, the then distorted flexible members 30 return to the position shown In FIG. 1 entering the holes 28 in the walls 26 with which they are then aligned. The alignment hole 3 is approximately one centimeter in diameter. The holes 28 are approximately one-half centimeter in diameter.

Initially, with the guide inserted, adjustment of the plate 25 will be made by the patient or a medical technician in order to register the alignment hole 3 with the urinary meatus 16. Thereafter, adjustment is not necessary and the guide may be used by the patient on a regular basis.

Referring next to FIGS. 3–5, another embodiment of the invention will be seen. The guide G is of thin wall construction and has a handle 4, which may be of any convenient size and shape, and vaginal insert I. The insert has a convex upper surface 40 when measured transversely as shown in FIG. 5. The upper surface 40 or, surface proximal the guiding portion, is also concave as viewed in FIG. 3 as measured along a continuous line 42 lying in the upper surface and proceeding from the tip 44 to its terminus 46. The underside 43 of the insert on the side distal the guiding portion is concave as seen in FIG. 5 with its edges 47 terminating in a plane 48. The surface 43 may be flat, i.e. lying in the plane 48. A plurality of guide holes 3 are formed in the concave portion which is also known as the guiding portion.

It will be seen that the guide holes 3 have their axes parallel to each other as viewed in FIG. 3 and and are linearly aligned one above each other as viewed in FIG. 4 in the curvilinear portion of the guiding portion 19. They are located along the concave arcuate line 42 on the insert. Accordingly, the lowermost hole 47 is closer to the toe or tip 44 than the uppermost hole 49.

In practice, the insert portion 1 of the guide shown in FIG. 3 is inserted in the vagina with its lower or flat surface 43 resting on the interior wall of the vagina 6 whether or not the surface is concave or flat. The concave portion 42 of the guiding area engages the pubic area immediately surrounding the urethral meatus, the folds of the skin, the labia majora and labia minora having been lifted out of the way. The catheter 14 is then inserted through whichever guide hole 3 which aligns with the meatus 16.

Referring next to FIGS. 6–8, another embodiment of the invention will now be described. As in the prior embodiments, the guide G includes a handle 4 and an insert portion 1 extending from the guiding portion 19. The insert 1 and the guiding portion 19 are arrayed to form an obtuse junction of of more than 90°. A baffle 50 is located in the guide portion 19 as seen in FIG. 8. The insert portion 1 has a concave inner surface 52 proximal the guiding portion 19 and a convex outer surface 54 distal the guiding portion 19. Its upper edges 56 lie in a plane 58. The surface 52 may also be flat i.e. lying in the plane 58.

The baffle wall 50 which is flat and includes a plurality of guide holes 3 arranged with their axis in vertical alignment as seen in FIG. 7 and in the said plane since the baffle is planar.

In operation, the insert portion 1 is placed in the vagina and the guide G is lifted slightly by the handle 4. One of the guide holes 3 becomes aligned with the meatus permitting a catheter 4 to be readily inserted.

After catheterization, both the guide and catheter are removed, the guide washed and put aside for subsequent use, the catheter washed or discarded The invention also contemplates a non-adjustable catheter guide having a single hole 3. The guide is one of a series of guides having guide holes 3 which vary in spacing from the insert portion 1. The invention also contemplates one or both surfaces of the guide portion 19 being flat.

I claim:

1. A device for use during female, intermittent, self-catheterization to assist in guiding a catheter into the urinary meatus comprising:

a. a hand held guide having a vaginal insert portion joined to a guiding portion; and
b. a plurality of linearly arranged guide holes in the guiding portion at least one hole of the plurality being alignable with the meatus when the insert is in the vagina through which aligned guide hole a catheter may pass.

2. A device according to claim 1 wherein the guiding portion is adjustable toward and away from the insert portion.

3. A device according to claim 1 wherein the surface of the insert portion proximal the guiding portion is concave.

4. A device according to claim 1 wherein the surface of the insert portion distal the guiding portion is convex.

5. A device according to claim 1 wherein the plurality of guide holes are formed in a flat surface of the guiding portion.

6. A device according to claim 1 wherein the plurality of guide holes are formed in a curvilinear surface of the guiding portion.

7. A device according to claim 1 wherein at least one surface of the guiding portion is flat.

8. A device for use during female, intermittent, self-catheterization to assist in guiding a catheter into the urinary meatus comprising:
a. a hand held guide having a vaginal insert portion joined to a guiding portion;
b. a plurality of linearly arranged guide holes in the guiding portion at least one hole of the plurality being alignable with the meatus when the insert is in the vagina through which aligned guide hole a catheter may pass; and
c. a handle joined to the guiding portion, the insert portion and the handle constituting opposite ends of the hand held guide.

9. A device according to claim 8 wherein the guiding portion is adjustable toward and away from the insert portion.

10. A device according to claim 8 wherein the surface of the insert portion proximal the guiding portion is concave.

11. A device according to claim 8 wherein the surface of the insert portion distal the guiding portion is convex.

12. A device according to claim 8 wherein the plurality of guide holes are formed in a flat surface of the guiding portion.

13. A device according to claim 8 wherein the plurality of guide holes are formed in a curvilinear surface of the guiding portion.

14. A device according to claim 8 wherein at least one surface of the guiding portion is flat.

15. A device for use during female, intermittent, self-catheterization to assist in guiding a catheter into the urinary meatus comprising:
a. a hand held guide having a vaginal insert portion joined to a guiding portion at an obtuse junction;
b. a plurality of linearly arranged guide holes in the guiding portion at least one hole of the plurality being alignable with the meatus when the insert is in the vagina through which aligned guide hole a catheter may pass; and
c. a handle joined to the guiding portion, the insert portion and the handle constituting opposite ends of the hand held guide.

16. A device according to claim 15 wherein the guiding portion is adjustable toward and away from the insert portion.

17. A device according to claim 15 wherein the surface of the insert portion proximal the guiding portion is concave.

18. A device according to claim 15 wherein the surface of the insert portion distal the guiding portion is convex.

19. A device according to claim 15 wherein the plurality of guide holes are formed in a flat surface of the guiding portion.

20. A device according to claim 15 wherein the plurality of guide holes are formed in a curvilinear surface of the guiding portion.

21. A device according to claim 15 wherein at least one surface of the guiding portion is flat.

* * * * *